United States Patent
Broadley et al.

(10) Patent No.: US 8,047,735 B2
(45) Date of Patent: Nov. 1, 2011

(54) APPLICATOR TIP FOR APPLYING SURGICAL GLUE

(75) Inventors: Kenneth N. Broadley, Naas (GB); Michael Mulvey, Ratoath (IE); Nico Zinndorf, Langenfeld (DE)

(73) Assignee: Henkel AG & Co., KGaA, Duesseldorf (DE)

( * ) Notice: Subject to any disclaimer, the term of this patent is extended or adjusted under 35 U.S.C. 154(b) by 0 days.

(21) Appl. No.: 12/624,468

(22) Filed: Nov. 24, 2009

(65) Prior Publication Data

US 2010/0104349 A1 Apr. 29, 2010

Related U.S. Application Data

(63) Continuation of application No. PCT/EP2008/054850, filed on Apr. 22, 2008.

(30) Foreign Application Priority Data

May 24, 2007 (EP) .................................... 07010343

(51) Int. Cl.
*B43K 1/06* (2006.01)
(52) U.S. Cl. .............. 401/265; 401/193; 401/5; 132/116
(58) Field of Classification Search .............. 401/5, 193, 401/295, 266, 265; 132/112, 113, 116
See application file for complete search history.

(56) References Cited

U.S. PATENT DOCUMENTS

| | | | | |
|---|---|---|---|---|
| 2,293,634 | A | * | 8/1942 | Sluss .............................. 132/113 |
| 4,044,724 | A | * | 8/1977 | Merchill ....................... 119/605 |
| 4,143,667 | A | * | 3/1979 | Peilet .............................. 401/28 |
| 4,875,602 | A | | 10/1989 | Chickering et al. |
| 5,882,133 | A | * | 3/1999 | Chao et al. .................... 401/266 |
| 2003/0191476 | A1 | | 10/2003 | Smit |

* cited by examiner

*Primary Examiner* — David Walczak
(74) *Attorney, Agent, or Firm* — David P. LeCroy (57) ABSTRACT

Applicator tip for applying fast curing adhesive of low viscosity to a surface. The applicator tip comprises a body with an inner canal for feeding the adhesive to an orifice. Spikes in various shapes and placements are arranged around the orifice for preventing the orifice from contacting the surface.

18 Claims, 12 Drawing Sheets

APPLICATOR TIP FOR APPLYING SURGICAL GLUE

CROSS REFERENCE TO RELATED APPLICATIONS

The present application is a continuation of International Application No. PCT/EP2008/054850, filed 22 Apr. 2008, which claims the benefit of European Patent Application No. 07010343.7, filed 24 May 2007.

The invention relates to an applicator tip and to a method of using the applicator tip for applying a fast curing adhesive, for example, a cyanoacrylate adhesive.

The use of fast curing adhesives has become popular for bonding or adhering small pieces of various materials. Commonly fast curing adhesives are often referred to as superglue, because they need only seconds for curing when applied to a surface.

One example of a fast curing adhesive is based on cyanoacrylate, which is the generic name for substances such as methyl-2-cyanoacrylate or 2-octyl cyanoacrylate or n-butyl cyanoacrylate. These fluid cyanoacrylate-based adhesives are monomeric until they turn into a polymer in a polymerization process. The polymerization process of the monomeric compound can be initiated by various substances. Usually the polymerization process is initiated by water, specifically hydroxide ions contained in water, such that the polymerization process is started once the cyanoacrylate is applied to a moist surface. Another property of cyanoacrylate is the quick setting, often in less than a minute, and the full strength is reached after two hours.

Besides the well-known use of cyanoacrylate adhesives for bonding small parts in everyday life the use of fast curing cyanoacrylate adhesives has become widespread for medical use, because it has shown advantageous characteristics when bonding human or animal tissue.

Wounds can be closed with the adhesive instead of sutures, resulting in less pain to the patient. In addition, the polymerized cyanoacrylate can act as a microbial barrier and may therefore decrease the risk of infection.

The adhesive can be used topically to close skin incisions and lacerations alone, or it can be used in connection with deep sutures. Generally, the adhesive can be used in place of non-absorbable sutures for primary closure of skin incisions and lacerations on the face.

On the surface the adhesive is applied to for closing a skin incision or laceration, that is the human or animal tissue, the polymerization will start almost instantaneously, that is the adhesive will cure at once, because there will be enough moisture to initiate the polymerization. Accordingly care must be taken when applying the adhesive.

A plurality of applicators and applicator tips has been developed for applying fast curing adhesives to tissue. As only small amounts of adhesive need to be applied they have in common that they are designed for applying these small amounts. As it is desirable to apply the adhesive under sterile conditions they have been designed for one-time use.

For example, U.S. Pat. No. 4,875,602 describes a liquid dispensing apparatus comprising a small deformable container holding the adhesive. On applying the liquid adhesive it is forced through a transportation canal to the applicator tip, for which different designs are described. A first design describes a cotton swab in a rounded, oval form as fluid applicator element. A second design depicts a brush as applicator, such that the adhesive at least partially travels through the swab or along the hairs of the brush before applied to the surface, such that the adhesive is applied directly by the swab or brush touching the surface (i.e., the tissue).

Touching the surface to which the adhesive is to be applied may be disadvantageous in cases where the surface because of its moisture starts the process of polymerization instantaneously. The curing adhesive may cure at the very surface of the swab or may glue the hairs of the brush. In particular when moving the applicator tip along the surface it will contact the moisture at the front portion, i.e. at the front portion in the direction of the movement. The adhesive contacting the moisture at the front portion may have sufficient time to cure while being transported to the end of the tip, such that the curing adhesive forms a sealing surface on the swab or glues the hairs of the brush together.

Using an applicator tip without a swab or a brush or something alike may alleviate these problems. An applicator tip comprising a hollow needle serving having an orifice at its end is known. However a small orifice allows applying a small line of glue only whereas a swab or brush allows spreading of the adhesive. Also depending on how fast the adhesive cures there may be deposits of cured polymerized adhesive around the orifice or it may be clogged or closed at all.

Accordingly there is a need for an applicator tip for applying adhesive while avoiding or alleviating the above-mentioned problems.

According to a first aspect of the invention the problem is solved by an applicator tip for applying adhesive to a surface, the tip comprising a body portion with an inner tube for feeding the liquid to an orifice, characterized in that spikes protruding from the applicator tip are arranged in vicinity of the orifice.

Furthermore, a method is described for applying low viscosity, fast curing adhesive to animal or human tissue, wherein the adhesive is applied in a continuous movement forming a line or film of adhesive on the tissue, characterized in that the adhesive is applied using an applicator tip comprising a body portion with an inner tube for feeding the liquid to an orifice, wherein spikes protruding from the applicator tip are arranged in vicinity of the orifice.

DETAILED DESCRIPTION OF THE INVENTION

Figure 1:
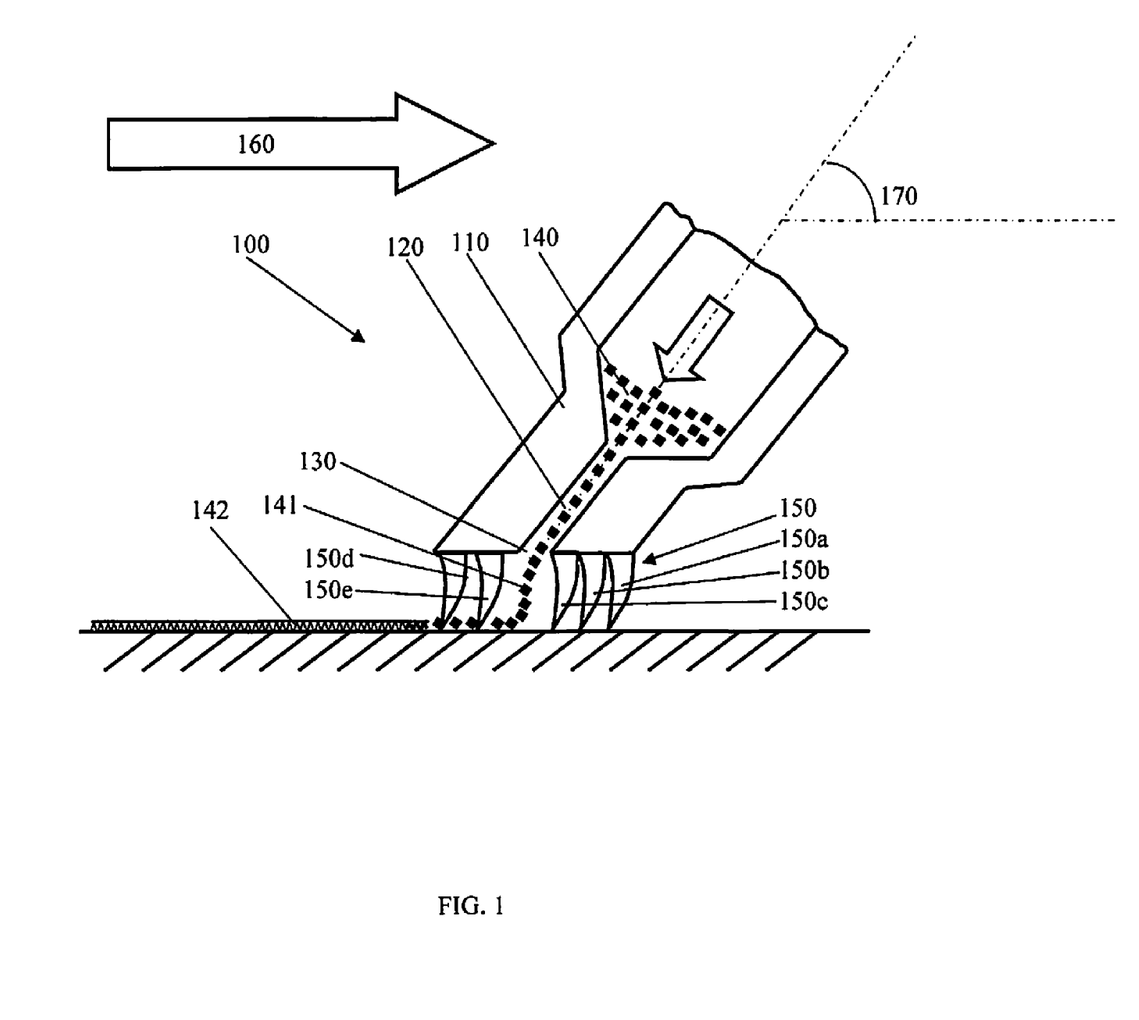
FIG. 1 depicts a schematic drawing of a cross section through an applicator tip when applying adhesive.

FIG. 1 schematically depicts a cross sectional view of an applicator tip 100 when in use (i.e., when applying adhesive to a surface).

The depicted applicator tip 100 comprises a body portion 110 to connect to or comprising a volume of adhesive. The applicator tip 100 may be attached to a separate container such as a collapsible tube. In particular, the applicator tip may be attached to a so-called monodose, which is understood as a container storing the amount of adhesive usually needed for a single average treatment. In one embodiment the container may be a container suitable for storing the adhesive under sterile conditions, such that the container is suitable for medical use. In an alternative embodiment the body may comprise a container, for example, a crushable container such as an ampoule, such that the container can be opened or crushed to release the adhesive when needed. The container is not shown in the drawing.

The applicator body portion 110 comprises an inner tube 120 ending in an orifice 130. The inner tube 120 feeds adhesive 140 from the container to the orifice 130. When the adhesive leaves the inner tube 120 through orifice 130, it will form a line of liquid due to its viscosity.

As the viscosity of the adhesive 140 is slightly higher than, for example, that of water, the adhesive 140 will form a continuous line 141 of liquid, which will be slightly more stable than a line of water output from an orifice. The viscosity of the adhesive 140 at 25° C. may be in a range of 1 to 1000 mPas, preferably in the range of 2 to 200 mPas, and most preferably in a range of 3 to 100 mPas, wherein the viscosity is measured using a Brookfield rotation-viscosimeter with spindle number 7 and 5 turns per minute.

Once the adhesive 140 leaves the orifice 130, it forms a continuous line 141 of liquid adhesive before it reaches the tissue, which in the present exemplifying embodiment serves as a surface to apply the adhesive on. When touching the tissue the adhesive will spread on the tissue, wherein the degree of spreading depends on the viscosity of the adhesive, the speed of curing and on the moisture already on the tissue. For example, the adhesive may spread to a wider area should it have a very low viscosity, tend to cure slowly and the tissue is covered with any other liquid. In this way the adhesive will form a thin film 142 covering a wide area. In contrast, the adhesive may form a thicker and smaller film in case the tissue surface is dry but provides sufficient moisture to initiate the polymerization process immediately, such that the adhesive will cure almost instantly when touching the tissue. In this way the area and the thickness of the adhesive film 142 covering the tissue surface can be influenced by adjusting the properties of the adhesive.

In order to maintain a distance between the tissue surface and the orifice the applicator tip comprises spikes 150 arranged in the vicinity of the orifice 130, wherein the spikes 150 may have various shapes and may be arranged in various configurations serving different purposes.

When applying the adhesive 140 to a tissue surface the person holding the applicator will apply very little pressure on the applicator in the direction of the normal of the tissue surface such that the spikes of the applicator tip gently touch the tissue surface. Usually the person will take care to apply only very little pressure, as the tissue surface may be bruised or otherwise injured. Application of the adhesive 140 may then be performed in a continuous movement in the direction of arrow 160, wherein the adhesive 140 will be forced out of the container, for example, by squeezing the container, and wherein the applicator is moved parallel to the tissue surface to apply a continuous film of adhesive on the tissue. Arrow 160 illustrates the moving direction.

The applicator tip and the comprised spikes may be manufactured as a single piece of any flexible material suitable for handling cyanoacrylates, for example of silicone having rubber-like properties. In particular the applicator tip may be made of translucent silicone rubber, such that the person applying the adhesive can watch the adhesive flowing through the inner tube of the applicator tip body, which allows exact dosing of the adhesive. The rubber-like properties enable the spikes to bend when pressed against the tissue surface, such that they do not prick.

According to the moving direction and the pressure on the applicator tip and the specific shape and properties of the spikes they may bend in a direction opposite to the moving direction.

With respect to the moving direction spikes may be placed in front of or behind the orifice. Accordingly spikes 150*a*, 150*b* and 150*c* are placed in front of the orifice and spikes 150*d*, 150*e* are located behind the orifice. Although the two dimensional drawing may suggest that spikes located behind the orifice touch the adhesive this may not necessarily be true, because these spikes may be located in front of or behind the paper plane of the drawing.

Furthermore, the body 110 of the applicator tip 100 can be bent with respect to the longitudinal axis of the spikes 150 such that the applicator body 110 including the inner canal is angled, as indicated by reference numeral 170, with respect to the tissue surface when using the applicator tip. In another aspect, the spike ends from a plane and the axis of the inner tube is arranged beveled to the normal of the plane. In a further aspect, the normal of the plane and the axis of the inner tube and angle of about 45°.

Figure 2A:
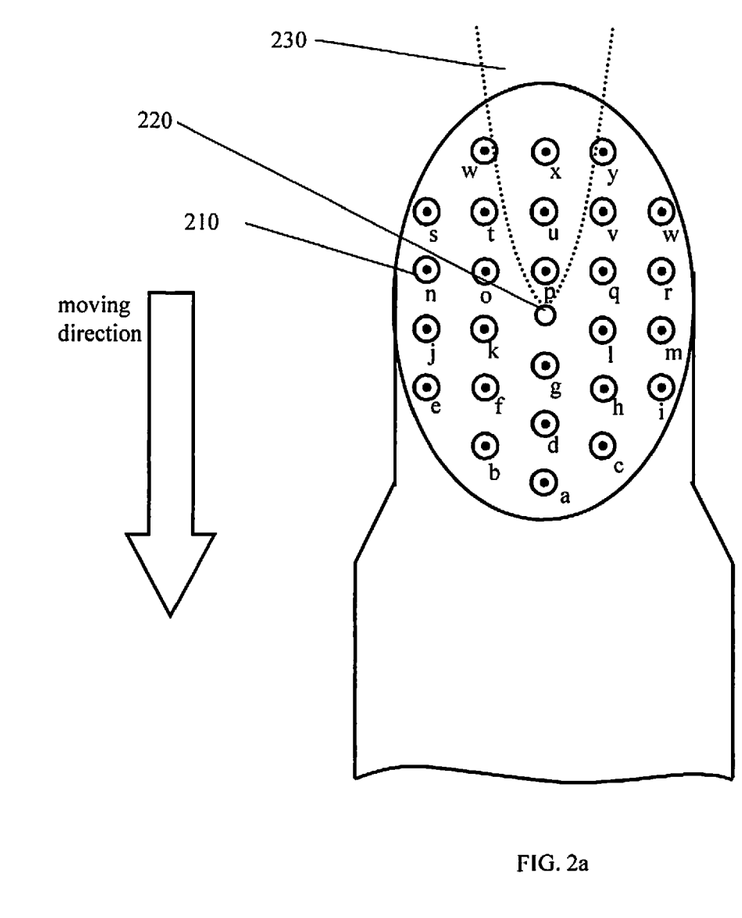
FIGS. 2a-c depict arrangements of spikes on the applicator tip.
Figure 2B:
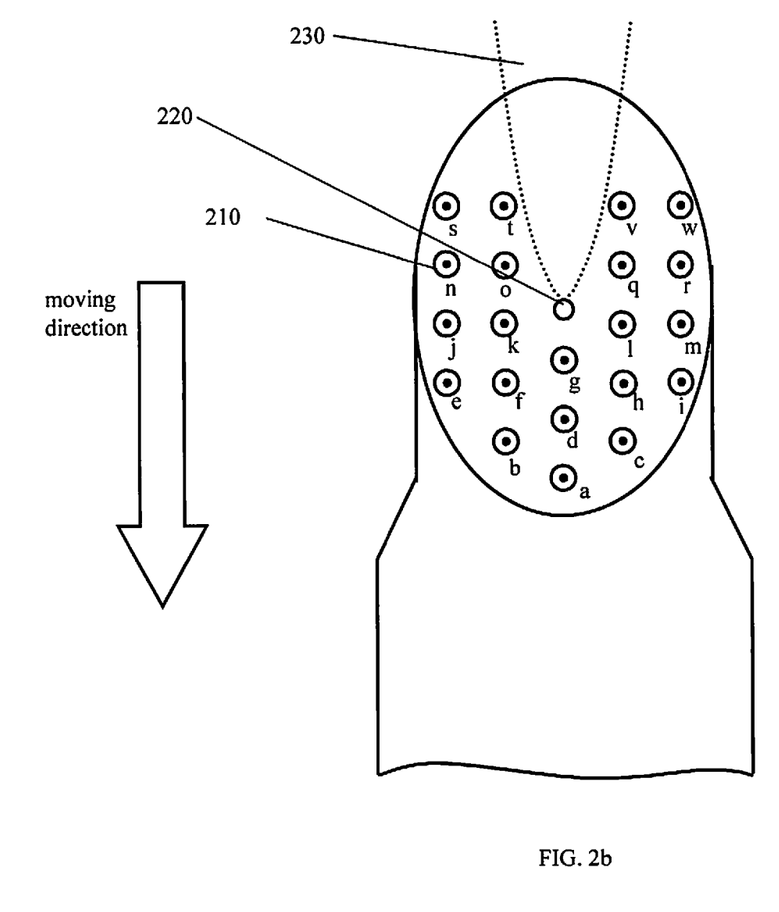
Figure 2C:
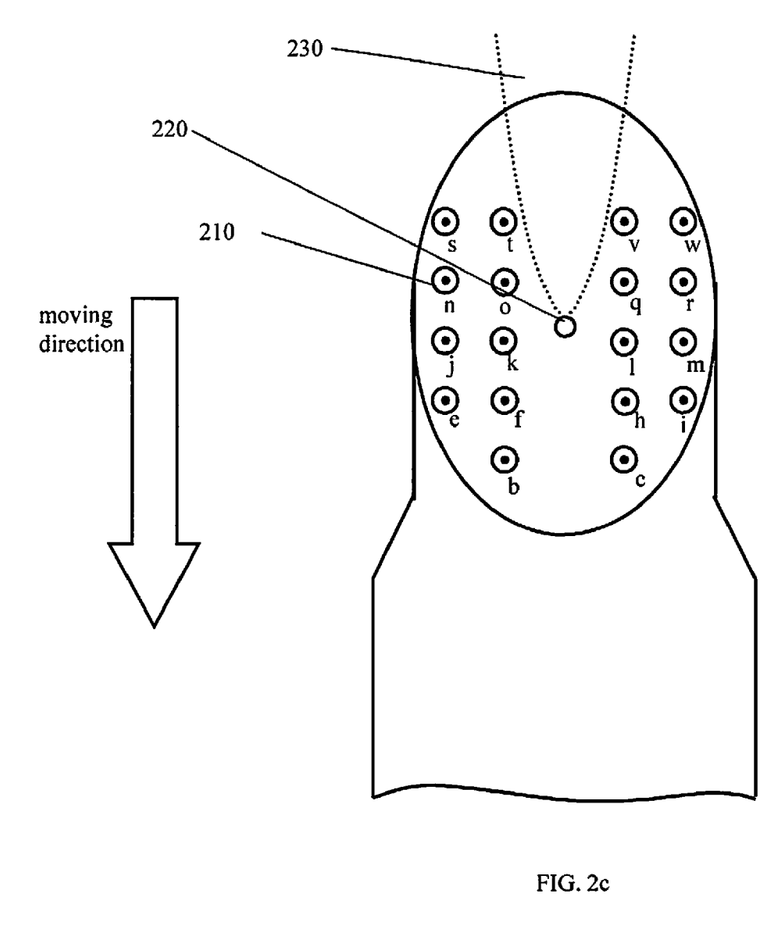

FIGS. 2*a* to 2*c* depict the bottom side of the applicator tip illustrating various arrangements of spikes 210 around the orifice 220. The arrow illustrates the direction of movement.

FIG. 2*a* depicts an embodiment of the applicator tip wherein the spikes 210 are arranged in columns parallel to the moving direction. Note that other arrangements, wherein the spikes are not exactly arranged in columns or rows are possible. With regard to the moving direction spikes 210*a* to *m* are arranged in front of orifice 220, whereas spikes 210*n* to *y* are arranged behind the orifice. In another embodiment not illustrated, the spikes can be arranged in a U-shape around the orifice. Here, the U-shape arrangement of the spikes can be such that the open end or top of the "U" forms an outlet for the liquid. In a further aspect, at least twice as many spikes are arranged at the closed end or bottom of the "U" arrangement.

Reference numeral 230 denotes the tissue surface area covered by the adhesive. This area may begin at the orifice 220, i.e., when applying the adhesive vertically below or behind the orifice 220 depending on the viscosity of the adhesive, the speed of the adhesive when it leaves the orifice 220 and the moving speed of the applicator tip across the tissue surface. The depicted shape and area size may serve as one example to illustrate that spikes 210 arranged behind the orifice 220 may be moved through the just dispensed adhesive. In particular at least spikes 210 arranged in a column of the moving direction including the orifice 220, i.e., in this embodiment spikes 210*p*, *u* and *x* might contact the adhesive.

Spikes 210 moved across the adhesive covered area may be assigned a different function than those moved outside said area and may accordingly have a different design. For example, the spikes 210 moved through adhesive may be designed to mix the adhesive with any liquid already on the tissue surface, for example, for accelerating the polymerization process.

In contrast to that spikes outside the adhesive covered area may be designed to work as spacers for maintaining a predefined distance between the tissue surface and the orifice in order to prevent that the adhesive mixes with any liquid covering the tissue surface and which could initiate the polymerization process, such that the orifice would be clogged by curing adhesive.

FIG. 2*b* depicts a variation of the arrangement of spikes shown in FIG. 2*a*. In this embodiment there are no spikes 210 that might contact the dispensed adhesive, i.e., spikes 210*u*, *w*, *x* and *y* have been removed. Note that depending on the above mentioned properties of the adhesive, the tissue surface and the parameters of applying the adhesive spikes 210t and v may come into contact with the adhesive, such that in variations of the arrangement these spikes could be omitted.

FIG. 2c shows a further variation of an arrangement of spikes 210, wherein spikes 210 in front of the orifice 220 and in the column including the orifice 220 are removed. This variation may be useful for example when treating a very sensitive tissue surface, wherein a contact of the tissue surface to any object should be avoided. For example, when sealing bruises on the skin with adhesive the surface is very sensitive to any contact, because a contact may be painful and may further damage the tissue. Considering the fact that the area of bruises is larger than the applicator tip, it may not be possible to prevent any contact. However reducing the number of spikes will help. In particular spikes arranged in the column including the orifice will irritate the tissue surface right before the adhesive is dispensed on the surface, which should be avoided.

Note that in similar arrangements the number of spikes can be further reduced to minimize any irritation caused by the touching of the spikes. For example in one arrangement only the outside columns can be retained, such that the distance between the orifice and the spikes 210 is maximized, i.e., spikes 210e, j, n and s are retained in one column and spikes 210m, r and w are retained in a column on the opposite side of the orifice 220. Furthermore the number of remaining spikes can be further reduced and arranged to further minimize any irritation, i.e., in one embodiment only two spikes 210, for example, e and i are maintained, such that when considering the moving direction the spikes are not arranged in a column to prevent touching the tissue surface by two or more spikes scratching consecutively in one column.

In this way the arrangement of spikes at the applicator tip can be adapted to various purposes.

FIGS. 3a to 3d schematically depict embodiments of spike shapes, wherein the drawings are not to scale and represent the concepts of the spikes. The depicted shapes of the spikes in this and all following drawings may vary with regard to their proportions. Accordingly the height of the spikes may be greater or smaller such that the spikes become slender or thicker.

Figure 3A:
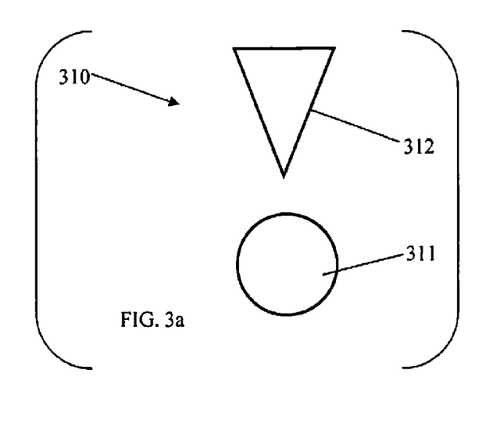
FIGS. 3a-3d depict basic shapes of spikes.

FIG. 3a shows a very basic shape of a spike 310, wherein the spike is shaped as a cone having a circular base area 311 and a straight directrix 312, such that the spike is shaped as a rotational solid. Accordingly this spike does not have any preferred direction for bending, in case the applicator tip is pressed against the tissue surface and moved in any direction.

Figure 3B:
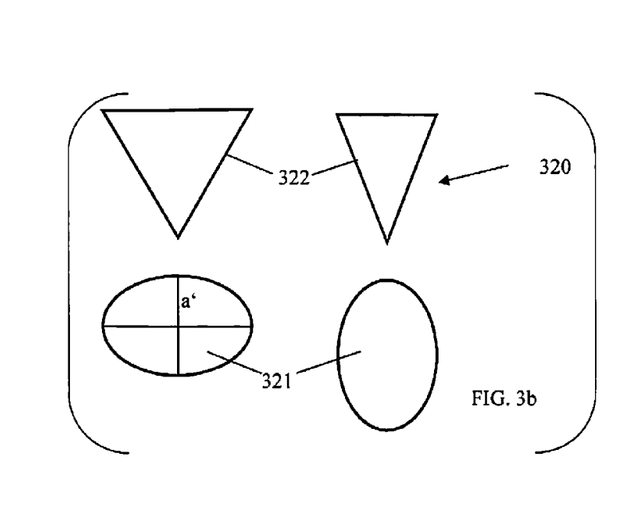

Spike 320 is a first variation having a straight directrix 322, but an oval base area 321. Accordingly this spike bends easier, i.e., less power is needed, in the direction of the short axis a' of the oval and bends harder in the direction of the remaining longer axis of the oval, i.e. a stronger force is needed to bend the spike in the direction of the longer axis of the base area.

Figure 3C:
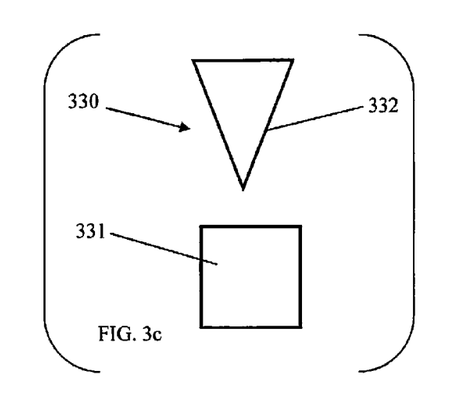
Figure 3D:
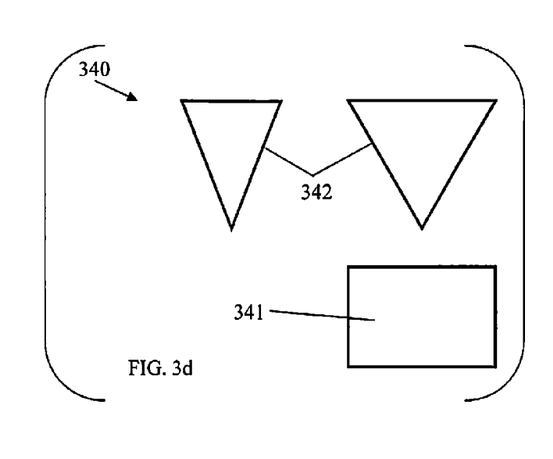

Spikes 330 and 340 as exemplified in FIGS. 3c and 3d depict spikes having straight having straight directrices 332, 342 and a square base area 331 or a rectangular, non-square base area 341 respectively. In contrast to the afore described spikes having a rounded base area, these spikes 330, 340 bend easier in a direction parallel to an edge of the base area but need a stronger force for bending in any other direction, in particular, diagonal to the edges of a base area. Furthermore, it is apparent that the spike having the rectangular, non-square base area bends easier in the direction of the short axis of its base area. In one aspect, the rectangular spike ends have a base area wherein the longer edge of the base area is arranged perpendicular to the direction of the inner tube.

Figure 4A:
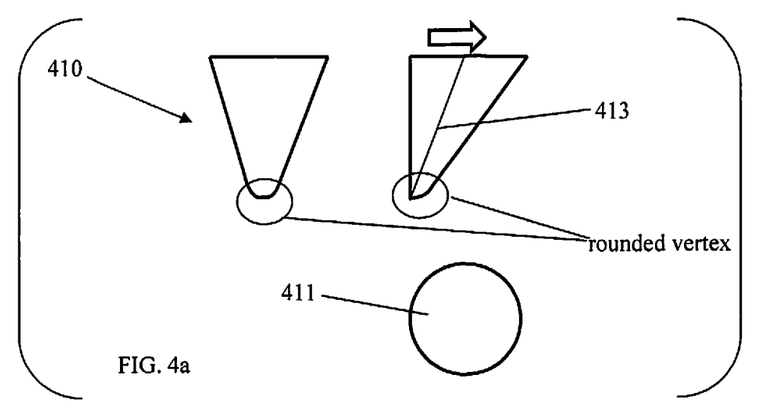
FIGS. 4a-4b depict shapes of spikes.
Figure 4B:
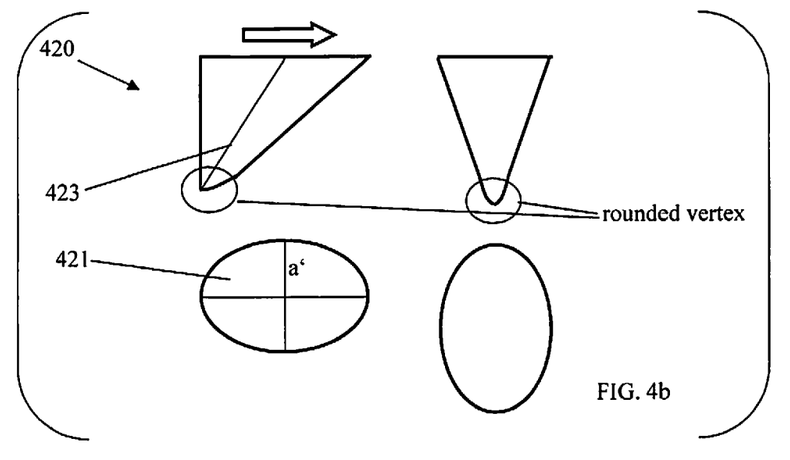

FIGS. 4a and 4b depict beveled cones 410 and 420, i.e., the axis 413, 423 from the gravity center of the base area to the tip of the cone is beveled with respect to the normal on the base area. Furthermore the tips of the cones are rounded, such that these cones do not tend to scratch on the tissue surface when moved in the direction as indicated by the arrow and also do not tend to bend in this direction because of their beveled shape. Instead these spikes will softly glide on the surface and thus cause less irritation when compared to the spikes of FIG. 3.

Spikes having a beveled shape may have a circular base area 411 such as spike 410 or an oval base area 421 such as spike 420 or may have rectangular base areas. The properties of a square or rectangular base area are analogous to that described with reference to FIGS. 3a-3d.

FIG. 5a-5d depict spikes having non-straight directrices, 512, 522, 532, 542, such that the spikes may have a more obtuse and rounded or more spiky and slim design.

Figure 5A:
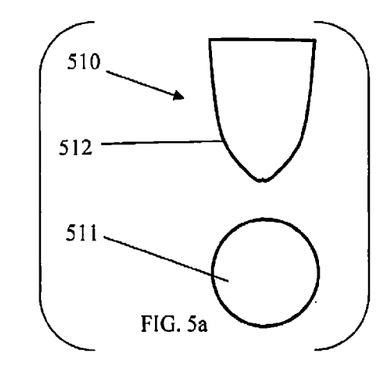
FIGS. 5a-5d depict shapes of spikes.

Spike 510 depicted in FIG. 5a has a circular base area 511, a convex directrix 512 and a rounded vertex, such that the spike has an obtuse rounded shape. Apparently, this spike does not tend to scratch when moved across a sensitive tissue surface and also does not tend to bend easily due to its massive design.

Figure 5B:
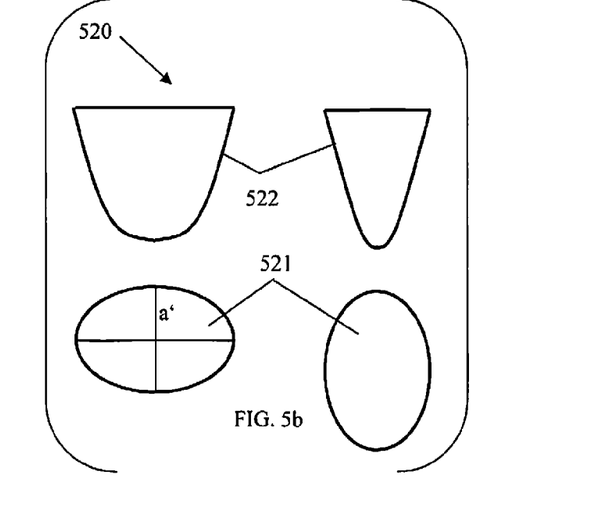

Spike 520 as shown in FIG. 5b is of similar design, but has an oval base area 521 effectuating that the spike can be bend more easily in the direction of the short axis a' than in the direction of the longer axis.

Spikes having convex curved directrices may also have square or rectangular, non-square base areas, wherein these base areas basically introduce the properties described above for these shapes of a base area. Also these spikes may be beveled, such that the properties described above and caused by a beveled design are added to the spikes.

Spikes having convex curved directrices 512, 522 and a rounded vertex are suited for being used to maintain a predefined distance between the tissue surface and the orifice.

Figure 5C:
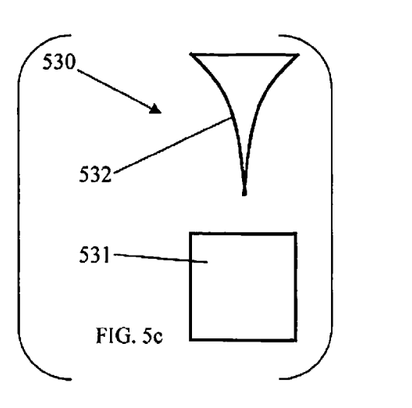
Figure 5D:
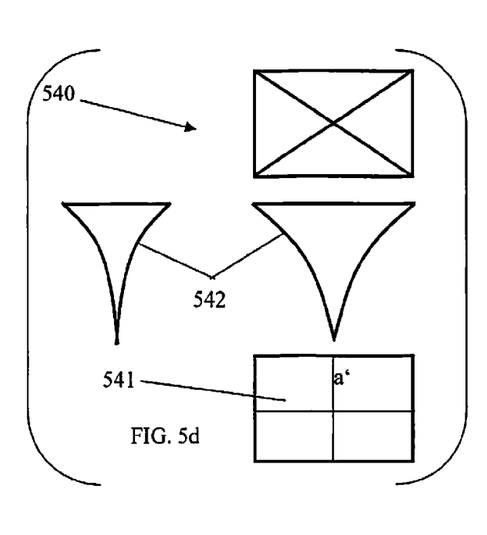

FIGS. 5c and 5d depict spikes 530, 540 having a concave curved directrix 532, 542 causing a slim design and a spiky vertex. Due to their slim design they tend to bend easily in any direction, wherein the spike as shown in FIG. 5d bends more easily in the direction of the short axis a'. Although the depicted embodiments have a square 531 and a rectangular 541 base area, respectively, it is apparent that they can also have a circular 511 or oval 521 base area. For example, a circular base area 511 will not have any preferred direction for bending and thus may have properties like hairs of a brush.

As these slim shaped spikes 530, 540 tend to bend easily, i.e., when applying a small force, they can be placed behind the orifice and can be used, for example, to mix the dispensed adhesive with a liquid on the tissue surface to initiate and/or accelerate the polymerization process.

Figure 6A:
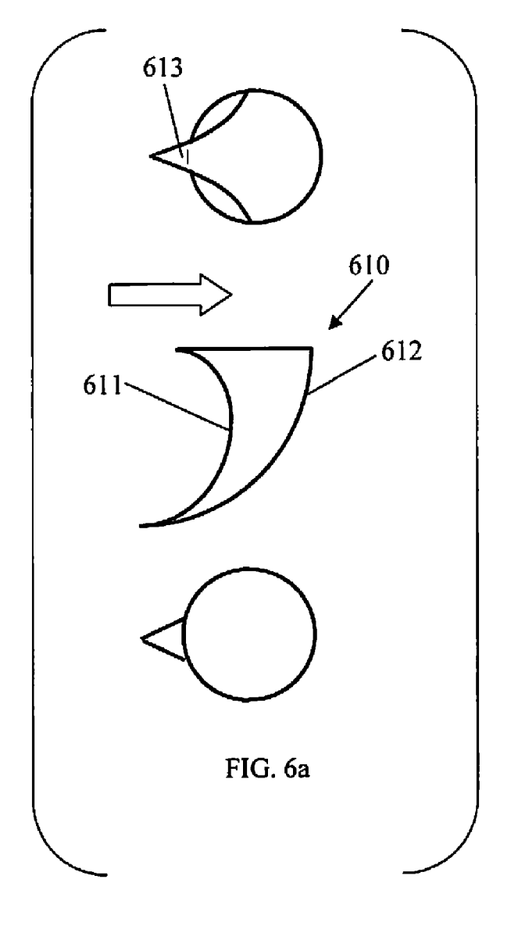
FIGS. 6a-6b depict specific non-irritating shapes of spikes.
Figure 6B:
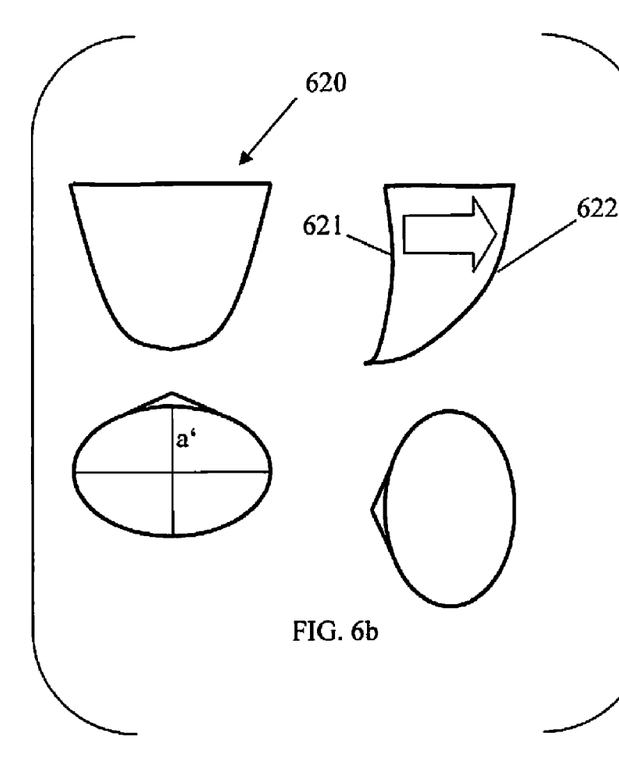

FIGS. 6a and 6b depict embodiments of spikes 610 and 620 having a fin-like shape, i.e., one concave curved directrix 611, 621 and an opposite convex curved directrix 612, 622, respectively, wherein the directrices of spike 6a are more curved than that of FIG. 6b, which effectuates a more streamline design.

Due to its slim and curved design, the spike shown in FIG. 6a will glide easily across a sensitive tissue surface when moved in the direction indicated by the arrow but will bend easily when applying a force vertical to the tissue plane and will thus not prick. Accordingly a spike of this design will only cause very little irritations on a sensitive tissue surface. A spike like this can be located behind the orifice in order to mix or spread the dispensed adhesive. In particular, for spreading the adhesive the spikes can be arranged such that tails of spikes in an outer column may be directed to the outside in order to increase the area covered by the adhesive.

In contrast, the spike shown in FIG. 6b can take a stronger force before bending, while still shaped to easily glide across a tissue surface without causing irritations. Accordingly, spike 6b is suitable to be arranged in front of the orifice with the purpose of maintaining a predefined distance between the tissue surface and the orifice.

In another embodiment depicted in FIG. 7a-7f, a spike can be adapted to give a tactile feedback signal to the user when applying excessive pressure on the applicator tip. To achieve this, the spike is designed to fold when the vertical pressure applied exceeds a threshold. The spike is designed to be hollow, such that it has an excavation inside allowing the material of the directrix to fold into the excavation.

Figure 7A:
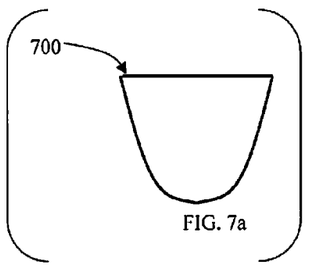
FIGS. 7a-7f depict an embodiment of a hollow spike.
Figure 7B:
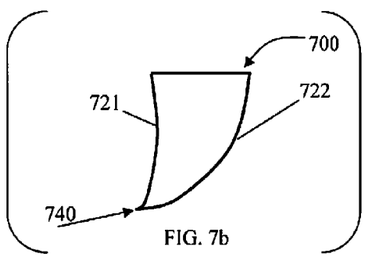

FIG. 7a depicts a front view and FIG. 7b depicts a side view of a spike 700 having an outer shape similar to that of the spike depicted in FIG. 6b. Due to its curved design the spike easily glides over a surface in a direction indicated by arrow 710 and in one embodiment may be arranged in front of an orifice, such that when moving the applicator tip while dispensing the adhesive the spike only serves as a distant control.

Figure 7C:
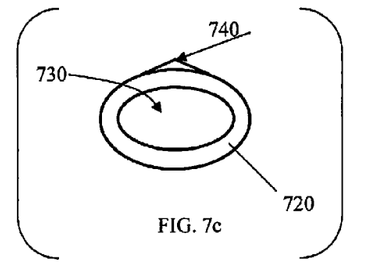
Figure 7D:
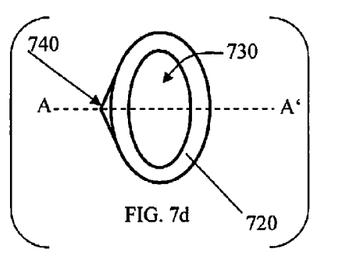

FIGS. 7c and 7d depict top views on the spike. Unlike spikes depicted in previous described embodiments, in this embodiment the spike 700 is designed to have a sidewall 720. The spike thus is hollow such that the sidewalls surround an excavation 730. At the top of the spike 700, sidewall 720 is shaped to an oval shaped ring. The vertex 740 of spike 700 is formed by the merging sidewalls 720.

Figure 7E:
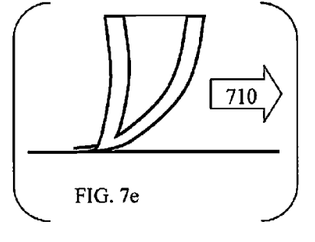

When starting to apply a vertical force 750, i.e., a force directed vertical to the surface the adhesive is applied on, the spike will start to bend such that the curvature of the sidewalls increases depending on the strength of the force. FIG. 7e depicts a cross sectional view along cut-line A-A' seen in FIG. 7d, when applying a very small vertical force on spike 700.

Figure 7F:
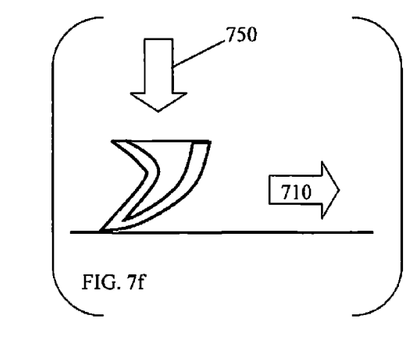

Unlike the spikes designed solid and as described above this hollow spike will fold when the vertical force exceeds a threshold. In particular the sidewall at the rear 721 of the spike will fold into the excavation 730 as illustrated in FIG. 7f. Sidewall 722 at the front of the spike will accordingly bend more. So with increasing vertical force the spike will at first bend until the applied force exceeds a threshold causing the spike to fold abruptly. The spike may fold to an extent that the sidewalls 721 and 722 may touch each other such that the excavation is minimized.

When the spike folds abruptly the height of the spike decreases abruptly thus giving a tactile feedback to the user. A user applying a vertical force on the applicator in this way receives a tactile feedback indicating that the vertical force applied to the applicator and to the spikes at the tip of the applicator exceeded a threshold.

Note that spikes of all shapes described above can be designed to have sidewalls forming an excavation.

Figure 8A:
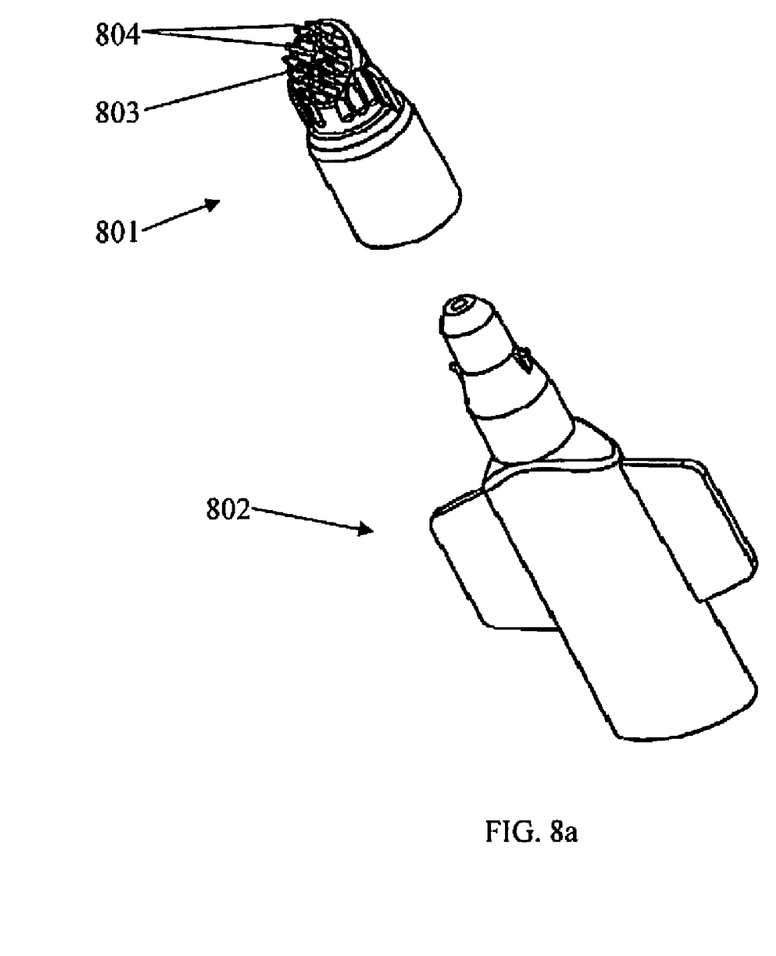
FIGS. 8a-8c depict an embodiment of an applicator tip and container.
Figure 8B:
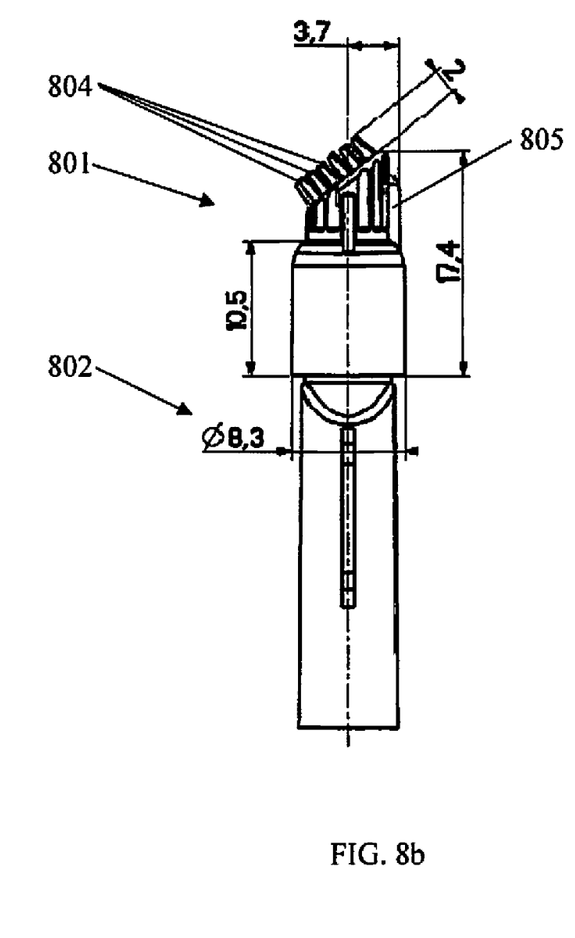
Figure 8C:
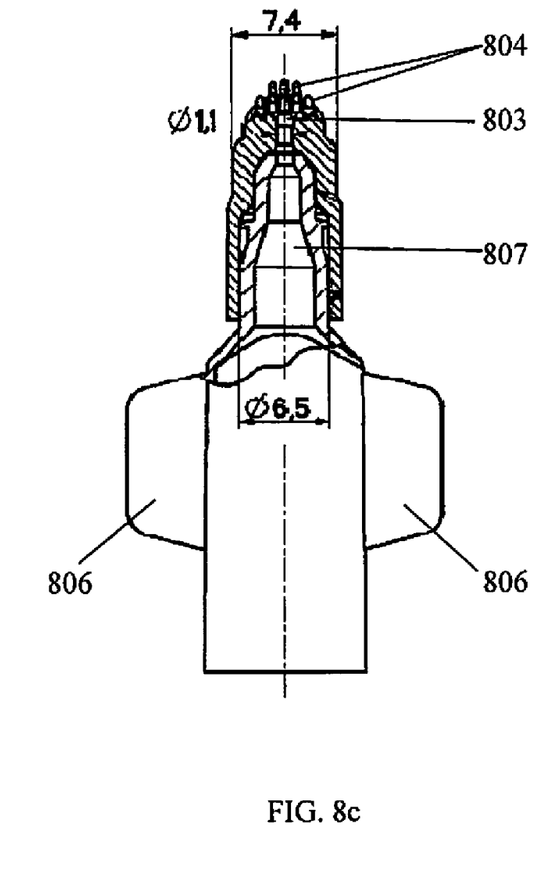

FIGS. 8a to 8c depict an embodiment of the applicator tip 801 and a container 802, which will be put into production. The dimensioning as given in the drawings are in millimeters and may serve as one example, other dimensions are possible.

FIG. 8a shows an applicator tip 801, which can be mounted to a container 802. As described above the container may hold a volume for a single treatment, such that the volume contained may be in the range between 0.5 ml to 5 ml. As any container suitable for holding fast curing adhesive of low viscosity, in particular a cyanoacrylate compound, may be used, the depicted container serves as one embodiment.

The applicator tip 801 may be slipped onto the tube shaped outlet of the container, wherein the flexibility of the material will provide a sufficient tight mounting. The tip comprises an orifice 803, which is nearly hidden by surrounding spikes 804. The spikes 804 are arranged around and close to the orifice 803.

In this embodiment the spikes are all identical and of simple cone shape. The spikes 804 protrude from a plate formed at the end of the applicator tip having the orifice 803 nearly in its centre. The plate at the end of the applicator tip is bevelled with regard to the longitudinal axis—see dotted line in FIG. 8b—such that people using the applicator tip will hold applicator at a corresponding angle to the tissue surface to be treated when applying the adhesive.

FIG. 8b depicts a side view on the applicator tip 801 mounted on the container 802, such that the applicator tip is stuck on the tube shaped outlet of the container. As indicated in the drawing the spikes have a length of 2 mm. Basically, the spikes may have a length of in the range of 0.5 mm to 10 mm, preferably in the range of 1 mm to 3 mm, wherein the spikes not necessarily must have the same length.

For example, in one embodiment a first group of spikes may have a first length, wherein the spikes are designed to maintain a predefined distance between the orifice and the tissue surface, for example, spikes as illustrated in FIG. 6b. Accordingly the length of these spikes defines the distance, wherein it is assumed that any deformation due to bending upon pressure of the applicator tip is negligible. This group of spikes preferably is arranged in front of the orifice or in a way such that dispensed adhesive will not contact a spike. A second group of spikes may be longer and of a design easily bending, for example, a design as illustrated in FIG. 6a. As the function of the second group of spikes may be to mix the dispensed adhesive with the liquid on the tissue surface or to spread the adhesive over a wider area, this group of spikes is arranged behind the orifice such that the spikes contact the dispensed adhesive. When applying the adhesive to the tissue surface, the first group of spikes will maintain the minimum distance between orifice 803 and the tissue surface, wherein it is assumed that spikes of the second group bend under the pressure applied to the applicator tip. This actually approximates the actual use, because a person using said applicator tip will be aware of the function of the second group spikes and will correspondingly perform a suitable pressure on the applicator tip.

FIG. 8b furthermore depicts a ridge 805 arranged on the topside of the applicator tip 801, which may serve as visual indicator for the person assembling and using the applicator tip and the container. As ridge 805 is positioned on top of the applicator tip and should be positioned aligned with the centre line of the wider flange of the container it indicates the correct attachment to the container, such that the arrangement of spikes is not twisted or canted with respect to the tissue surface.

FIG. 8c depicts a top view on the container 802 with the attached applicator tip, wherein the portion of the applicator tip and the incorporated tube shaped outlet of the container are illustrated in a cross sectional view. Upon applying the adhesive the container will be gently squeezed to force out the liquid adhesive. For example a person could hold the container wings 806 on his index and middle finger and could gently press his thumb on the container. The adhesive will be fed through the tube shaped outlet 807 of the container to the orifice 803 of the applicator tip.

Although the present invention has been described in detail, it is to be clearly understood that the same is by way of illustration and example only, and is not to be taken as a limitation. The spirit and scope of the present invention are to be limited only by the terms of any claims presented hereafter.

We claim:

1. Applicator tip comprising:
   an orifice through which adhesive forms a continuous line of liquid adhesive before being delivered for application to a surface,
   a body portion having an inner tube ending in the orifice for feeding the adhesive to the orifice, and
   one or more spikes protruding from the applicator tip and arranged in the vicinity of the orifice, each of the one or more spikes having a base area and a tip,
   wherein the one or more spikes maintain a distance between the orifice and the surface such that the orifice does not clog due to curing of the adhesive from mixing on the surface with any liquid that could initiate polymerization,
   wherein the orifice, body portion and one or more spikes of the applicator tip are manufactured as a single piece of flexible material,
   wherein the flexible material is silicone, and
   wherein the one or more spikes have a height of from 0.5 to 10 mm.

2. Applicator tip of claim 1, wherein at least one of the one or more spikes is cone shaped.

3. Applicator tip of claim 1, wherein at least one of the one or more spikes is in the shape of a beveled circular cone.

4. Applicator tip of claim 1, wherein at least one of the one or more spikes is pyramid shaped with a square base area.

5. Applicator tip of claim 4, wherein an axis from the center of the base area to the top of the pyramid is beveled.

6. Applicator tip of claim 1, wherein the base area is a non-square rectangle, the longer edge of said base area arranged perpendicular to the direction of the inner tube.

7. Applicator tip of claim 1, wherein the spikes are arranged in U shape around the orifice, such that the open end of the U forms an outlet for the liquid.

8. Applicator tip of claim 7, wherein the at least twice as much spikes are arranged at the closed end of the U form.

9. Applicator tip of claim 1, wherein the tips of the one or more spikes form a plane and the axis of the inner tube is arranged beveled to the normal of said plane.

10. Applicator tip of claim 9, wherein the normal of the plane and the axis of the inner tube form an angle of around 45°.

11. Applicator tip of claim 1, wherein the spikes have a height in the range of 1 mm to 3 mm.

12. Applicator tip of claim 1, wherein the spikes are hollow thus forming an excavation.

13. Method for applying low viscosity, fast curing adhesive comprising:
    applying adhesive to a surface using an applicator tip having
    an orifice through which adhesive forms a continuous line of liquid adhesive before being delivered for application to the surface,
    a body portion having an inner tube for feeding the adhesive to the orifice, and
    one or more spikes protruding from the applicator tip and arranged in the vicinity of the orifice, each of the one or more spikes having a base area and a tip,
    wherein the one or more spikes maintain a distance between the orifice and the surface such that the orifice does not clog due to curing of the adhesive from mixing on the surface with any liquid that could initiate polymerization,
    wherein the orifice, body portion and one or more spikes of the applicator tip are manufactured as a single piece of flexible material,
    wherein the flexible material is silicone, and
    wherein the one or more spikes have a height of from 0.5 to 10 m.

14. Method of claim 13, wherein the adhesive is applied in a continuous movement forming a line or film of adhesive.

15. Method of claim 13, wherein the viscosity of the adhesive is in the range of 1 to 1000 mPas.

16. Method of claim 15, wherein the viscosity of the adhesive is in the range of 2 to 200 mPas.

17. Method of claim 16, wherein the viscosity of the adhesive is in the range of 3 to 100 mPas.

18. Method of claim 13, wherein the spikes arranged at the applicator tip fold when a vertical force applied to the applicator exceeds a threshold.

* * * * *